United States Patent [19]
Ding et al.

[11] Patent Number: 5,518,718
[45] Date of Patent: * May 21, 1996

[54] NONIRRITATING NONIONIC TISSUE CLEANING COMPOSITIONS

[75] Inventors: Shulin Ding, Irvine; Thao T. Tran, Garden Grove, both of Calif.

[73] Assignee: Allergan, Inc., Irvine, Calif.

[*] Notice: The portion of the term of this patent subsequent to Oct. 12, 2010, has been disclaimed.

[21] Appl. No.: 234,318

[22] Filed: Apr. 28, 1994

Related U.S. Application Data

[63] Continuation of Ser. No. 74,318, Jun. 9, 1993, which is a continuation of Ser. No. 819,397, Jan. 10, 1992, Pat. No. 5,252,246.

[51] Int. Cl.$^6$ .................................................... A61K 31/74
[52] U.S. Cl. ................................ 424/78.04; 424/78.02; 514/912
[58] Field of Search ........................... 424/78.02, 78.04; 514/912

[56] References Cited

U.S. PATENT DOCUMENTS

| | | | |
|---|---|---|---|
| 4,407,791 | 10/1983 | Stark | 424/80 |
| 4,748,189 | 5/1988 | Su et al. | 514/781 |
| 5,110,493 | 5/1992 | Cherng-Chyi et al. | 514/413 |

*Primary Examiner*—Zohreh Fay
*Attorney, Agent, or Firm*—Walter A. Hackler

[57] ABSTRACT

A nonirritating, nonionic detergent surfactant composition suitable for application to and cleaning of sensitive tissue, including periocular and ocular tissue, having a low cytotoxicity and high cleaning ability includes a principal nonionic surfactant and at least one auxiliary nonionic surfactant present in the surfactant composition in sufficient amounts to increase the cleaning ability of the principal nonionic surfactant.

8 Claims, 2 Drawing Sheets

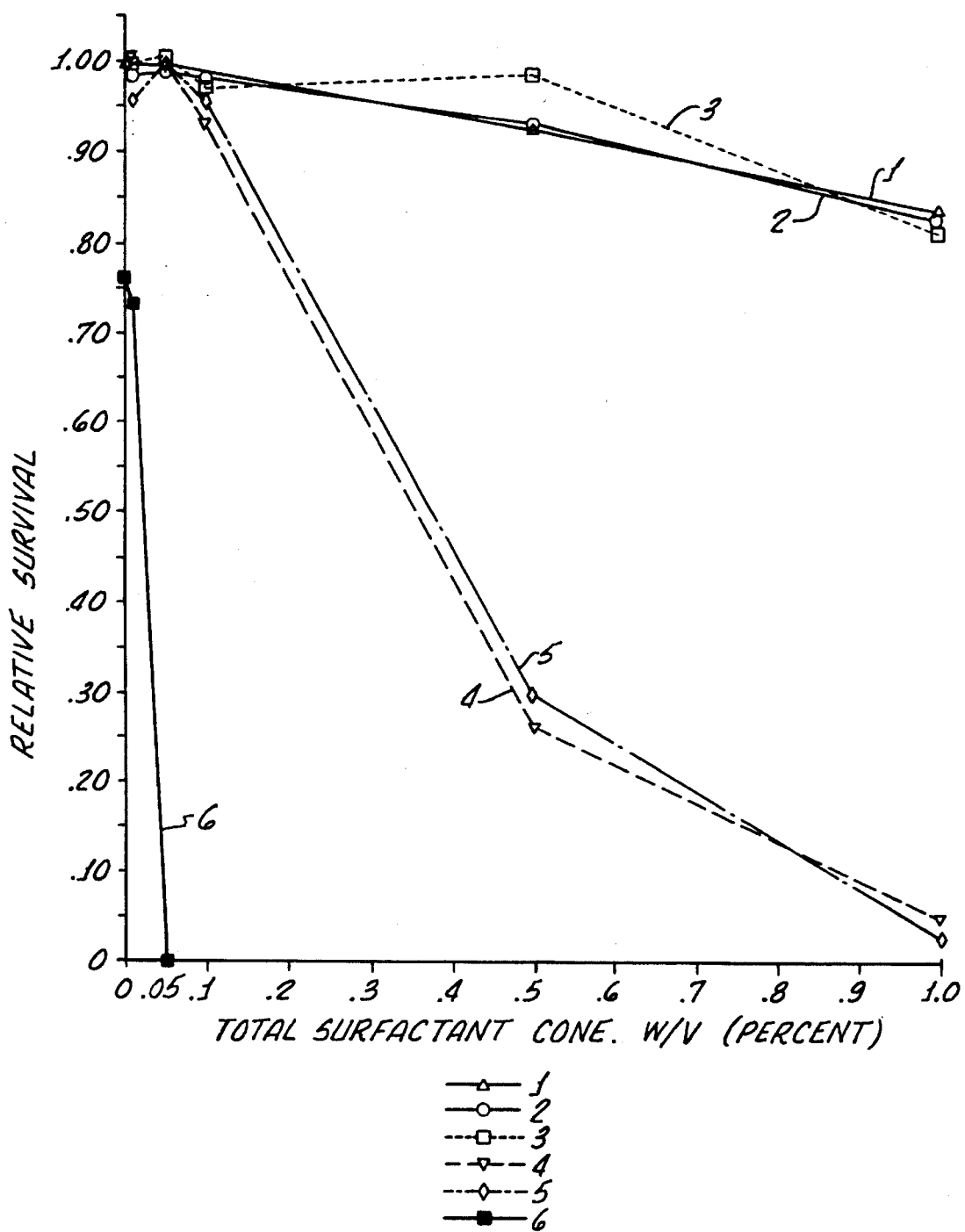

1

NONIRRITATING NONIONIC TISSUE CLEANING COMPOSITIONS

This application is a divisional application of Ser. No. 08/074,318, filed Jun. 9, 1993, now allowed, which is the continuation of Ser. No. 07/819,139, filed Jan. 10, 1992, now U.S. Pat. No. 5,252,246.

The present invention generally relates to detergent surfactant compositions suitable for application to and cleaning of sensitive tissues. More particularly, the present invention relates to non-irritating detergent surfactant compositions, comprised of a combination of nonirritating surfactants, especially suitable for lid hygiene in the treatment of chronic blepharitis.

The blepharitis, or inflammation of the eyelid, is a frequently encountered ocular disease. In addition to causing red and itching eyes, blepharitis may also interfere with the fitting of contact lenses, as well as aggravate the treatment of keratitis sicca, endanger intraocular surgery, or lead to corneal complications, such as toxic ephitheal keratitis catarrhal ulceration or phlycetnlosis.

One common symptom of blepharitis is a heavy deposition of oily debris called scurf on the eyelashes and lid margins. The oily debris is the secretion (meibum) of meibomian glands. In the blepharitis patients, it is often found that their meibomian glands suffer from oversecretion and/or a thickened meibum. As a result, the glands are engorged, clogged and inflamed.

The meibum is composed of various classes of lipids including a fatty wax/sterol ester fraction of up to sixty percent. This lipid component can enhance the accumulation of debris and crusting which further exacerbates inflammation associated with the blepharitis.

Lid hygiene is currently the most accepted treatment for blepharitis. In addition, a number of oral and topical medications may be utilized to augment the primary lid hygiene therapy as may be prescribed on an individual basis. Effective cleaning agents for removal of meibomian secretions associated with debris have been anionic surfactants having high foaming characteristics. See, for example, U.S. Pat. No. 5,000,868.

Unfortunately, such anionic surfactants tend to be irritating to sensitive ocular tissue and because of their ionic nature, may be chemically incompatable with other formulation ingredients such as, for example, buffers, preservatives and medicaments.

Consequently, surfactant compositions, specifically formulated for lid hygiene, have required the presence of surfactants capable of reducing the irritant properties of the anionic surfactant or reducing their chemical incompatability.

The composition of the present invention, effective for use on periocular and ocular surface tissues includes no component necessary for reducing irritating characteristics of other surfactant components.

SUMMARY OF THE INVENTION

The present invention is a nonirritating detergent surfactant composition suitable for application to and cleaning of sensitive tissues which is especially effective for cleaning of ocular and periocular tissue.

The composition comprises a principal nonionic surfactant present in the nonirritating detergent surfactant composition in a sufficient amount to clean the sensitive tissue. More particularly, the cleaning ability may be defined in terms of the lipid cleaning efficiency of the surfactant.

In addition, at least one auxiliary nonionic surfactant is present in the composition in a sufficient amount to increase the cleaning ability of the principal nonionic surfactant. It is important to appreciate that no irritating surfactants such as anionic surfactants are present in the composition of the present invention. Hence, there is no component of the composition of the present invention which is added to overcome or suppress the irritating activity of a component. This results in a naturally inherent nonirritating surfactant composition.

Importantly, the auxiliary surfactants present in the composition are effective for enhancing the cleaning ability of the principal auxiliary nonionic surfactant. In the instance where one auxiliary surfactant is used in conjunction with the principal nonionic surfactant, the cleaning ability of the resultant composition is greater than the cleaning ability of either the principal surfactant or the auxiliary surfactant taken alone. More particularly, this occurs when both the principal and auxiliary nonionic surfactants comprise block polymers of polyoxyethylene and polyoxypropylene. Specifically, this enhanced cleaning activity occurs when the principal nonionic surfactant comprises Pluronic® P85, (CTFA name: poloxamer 235) and the auxiliary nonionic surfactant comprises Pluronic® F87 (CTFA name: poloxamer 237).

The nonirritating detergent surfactant composition of the present invention further has extremely low irritation potential to ocular and periocular tissue. The low irritation potential of the composition of the present invention may be demonstrated with in vitro Chinese hamster ovary cell cytotoxicity test. Specifically, when the principal and auxiliary nonionic surfactants are present in the nonirritating detergent surfactant composition in a combined amount of at most ten percent by weight, and the composition applied to Chinese hamster ovary cells at a tenfold dilution, more than eighty percent of the cells survive.

BRIEF DESCRIPTION OF THE DRAWINGS

The advantages and features of the present invention will be better understood by the following description when considered in conjunction with the accompanying drawings in which:

FIG. 2 is a plot of relative survival of Chinese hamster ovary cells for the present invention, either unpreserved or preserved by five different preservative systems, showing the cytotoxicity profile thereof. The profile of an unpreserved anionic surfactant, disodium monolaureth sulfosuccinate, is also included for comparison.

DETAILED DESCRIPTION

Figure 1:
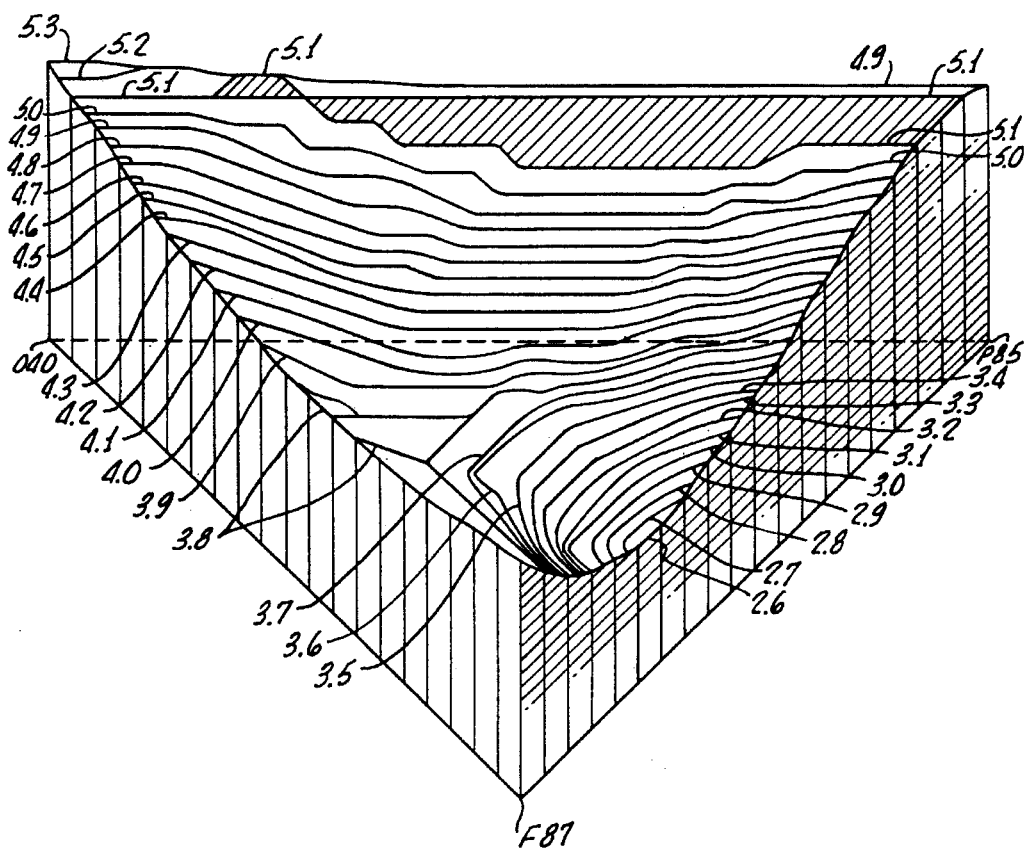
FIG. 1 is a three-dimensional representation showing the relative cleaning ability of compositions in accordance with the present invention having varying amounts of principal and auxiliary nonionic surfactants.

It has been well established that a surfactant which cleans better is usually more damaging to cells. For example, anionic surfactants are generally more efficient in removing grease and dirt but are also more irritating and have a high cytotoxicity profile.

Nonionic surfactants are known to be milder than anionic surfactants but heretofore have not demonstrated detergent activity on a par with anionic surfactants.

As hereinbefore briefly discussed, prior art formulations for lid hygiene have utilized anionic surfactants which have high cytotoxicity and irritation to sensitive surfaces. In combination with such ionic surfactants, a number of components have been utilized in an attempt to reduce the irritant properties of the ionic surfactants. Because of the inherent irritant activity of anionic surfactants, compositions incorporating such surfactants, even though compensating components are present, require complete and thorough rinsing of the compositions from ocular and periocular tissue due to the possibility of anionic surfactant remaining in contact with such tissue after use of surfactant and thereby causing high irritation.

In view of the fact that no component of the composition of the present invention is inherently irritating to periocular or ocular tissue, no rinsing of the composition following lid cleaning is required.

While the following description of the present invention is directed to use as cleansers for ocular and periocular tissue, because of its nonirritating and low cytotoxicity profile, the composition of the present invention is also suitable for the cleaning of skin, mucous membranes, wounds, contact lenses, and removal of makeup for eyes and facial tissue. In addition, its use may be extended to the cleaning of hands and fingers which would subsequently be in contact with eyes, wounds, or other sensitive areas.

The principal nonionic surfactant present in the composition of the present invention is a block copolymer of polyoxyethylene and polyoxypropylene which are available under the trade name Pluronic® marketed by BASF. Specifically, the principal nonionic surfactant is Pluronic® P85. A first auxiliary nonionic surfactant is also a block copolymer of polyoxyethylene and polyoxypropylene and specifically comprises Pluronic® F87. The principal surfactant is present in the composition in an amount from about four percent to about nine percent by weight.

The first auxiliary surfactant is added to enhance the cleaning ability of the principal surfactant which may be effected through better solubilization, emulsification, or wetting power. The preferred auxiliary surfactant, in accordance with the present invention, Pluronic® F87 is present in the composition in an amount from about 0.5 percent to about two percent by weight.

Preferably, a second auxiliary nonionic surfactant, such as ethoxylated octyl phenol, may be combined with the principal and first auxiliary surfactants. Specifically, the second auxiliary surfactant may be Igepal® CA 897 (CTFA name: octoxynol 40) marketed by Rhone-Poulenc.

Preferably, the total amount of surfactants in the composition of the present invention is ten percent or less of the total composition with the remaining component being water. It should be appreciated that the composition of the present invention may be buffered by any common buffer system such as phosphate, borate, acetate, and citrate with the pH and osmolarity adjusted in accordance with well-known techniques to proper physiological values.

In addition, if a preservative is desired, the compositions may be preserved with any well-known system such as benzyl alcohol with/without EDTA, benzalkonium chloride, chlorhexidine, Cosmocil® CQ, or Dowicil® 200.

Importantly, because of the nonionic nature of the surfactants of the present invention, no chemical incompatability is encountered even if a positively or negatively charged preservative is incorporated, such as quaternary ammonium salts. This also applies to buffers and other medicaments that may be used in combination with the composition of the present invention.

In addition, depending upon the use of the cleanser, amino acids, minerals, vitamins, or the like may be added to provide nutrition to skin or tissues. Further, moisturizers or emollients such as aloglycerine propylene glycol, hyaluronic acid, hydroxic propyl cellulose, or carboxy methyl cellulose may be added to soothe the skin. Specifically, when the composition is to be used in connection with cleaning wounds, medications may be added, such as antibiotics, antimicrobiocidal agents, anti-inflammatory agents, local anesthetics, anti-acne agents, etc., depending upon the specific activity desired.

A clear advantage of the present invention resides not only in its extremely low toxicity risk but also in its minimal chemical incompatibility with other ingredients (such as preservatives, buffers, medications, etc.) incorporated in the formulations. The minimal chemically incompatible risk is attributed to the position of no ionizable functional groups in the surfactants chosen in the present invention.

The cleaning ability, specifically the lipid cleaning ability, of the composition of the present invention is diagrammatically presented in FIG. 1 so as to illustrate the synergistic effect of nonionic surfactant combinations which, in the case of Pluronic® F87 and Pluronic® P85, results in a greater cleaning ability than the cleaning ability of either the Pluronic® F87 or P85 taken separately. In addition, as will be hereinafter demonstrated, the combination of the principal surfactant, Pluronic® P85, and auxiliary surfactants, Pluronic® F87 and octoxynol 40, provide lipid cleaning ability on a par with anionic surfactants but with no irritating properties and significantly less cytotoxicity.

The diagram as shown in FIG. 1 will be discussed in more detail after the following description of the protocol in determining the cleaning ability of the detergent surfactant in accordance with the present invention.

In order to show lipid cleaning ability of the composition of the present invention, an artificial lipid mixture was utilized which comprised thirty percent cholesteryl stearate, thirty-five percent lanolin, and thirty-five percent Miglyol® 810 (CTFA name: caprylic/capric triglyceride).

This mixture was supported on a polymacon (38/0) lens (Hydron) with the convex surface of the lens coated with the artificial lipid mixture by lightly touching the surface to the melted lipid and leaving the coated lens on a slide (convex surface facing up), for between ten to thirty minutes.

Thereafter, the composition to be tested was placed, five drops at a time, on the palm of a hand and the lens, with the convex surface facing down, rubbed in a circular motion in the composition for twenty seconds. Thereafter, the lipid remaining on the lens was officially observed.

The cleaning efficacy scoring system was as follows:

| | CLEANING EFFICACY TEST |
|---|---|
| SCORE | VISUAL OBSERVATION (after rubbing lens with tested composition) |
| 0 | Lens is totally coated with lipid |
| 1 | ⅙ of the lens is not covered by lipid |
| 2 | ⅓ of the lens is not covered by lipid |
| 3 | ½ of the lens is not covered by lipid |
| 4 | ⅔ of the lens is not covered by lipid |
| 5 | ⅚ of the lens is not covered by lipid |
| 6 | All lipid on the lens is gone |

The cleaning score, between 1 and 6, is plotted for various surfactant compositions in FIG. 1 for percentages of principal surfactant from 0 to 10%, first auxiliary surfactant from 0 to 10%, and second auxiliary surfactant from 0 to 10%. The remaining composition is water.

These number scores appear in FIG. 1, which is diagrammatically presented in order to show the increased cleaning ability of the composition when the primary surfactant Pluronic® P85 is between about 2% to about 9%, the first auxiliary surfactant Pluronic® F87 is present in the amount of between 0.5% to about 2%, and the second auxiliary surfactant octoxynol 10 is present in the amount of about 0.5% to about 5%. Each of the points displayed in FIG. 1 include a total surfactant weight of about 10%. To compare the composition of the present invention with the prior art lid hygiene formulations, the cleaning efficacy test, as hereinabove described, was performed on I-Scrub, distributed by Spectra. The results are shown hereinbelow:

| TEST SOLUTION | OBSERVED SCORE |
| --- | --- |
| Spectra's I-Scrub | 4.67,5.33,5,4.67,5.33 |
|  | Mean = 5.0, CV = 6.6% |
| The optimized formulation | 5.3,5 |

These results demonstrate that the optimized formulation of the present invention has the equivalent cleaning ability as that of I-Scrub, which is an anionic surfactant-based formulation.

The ingredients of I-Scrub are generally known as follows:

| I-SCRUB | |
| --- | --- |
| Disodium monolaureth Sulfosuccinate | anionic surfactant (mild, high foaming) |
| PEG-200 Glyceryl Monotallowate | nonionic surfactant (emulsifier, anti-irritant) |
| PEG-78 Glyceryl Monococcate | nonionic surfactant (emulsifier, anti-irritant) |
| Cocoamidopropylamine Oxide | nonionic surfactant (foam booster, anti-irritant) |
| Benzyl Alcohol, EDTA, Purified Water USP | preservative |

An important feature of the composition of the present invention is its low cytotoxicity profile. The cytotoxicity was evaluated as follows to quantify chemically-induced toxicity. Chinese hamster ovary cells used (CHO) are a well-characterized cell line and are widely used in cytotoxicity assays as has been well-documented in the literature.

The materials and methods of the present assay are as follows:

MATERIALS

A. CHEMICALS AND MEDIA
1. Ham's F-12 medium (1X, with sodium bicarbonate)
2. Heat inactivated fetal bovine serum (lots tested using SOP TC-003)
3. L-glutamine solution (200 mM)
4. Dulbecco's phosphate buffered saline (PBS)
5. Trypsin-EDTA solution (1X)
6. Sodium chloride
7. Sodium phosphate (monobasic and dibasic)
8. β-nicotinamide adenine dinucleotide phosphate (NADP)
9. Glucose-6-phosphate (Glc-6-P)
10. Potassium chloride
11. Magnesium chloride
12. Calcium chloride
13. Aroclor 1254 induced rat liver S9
14. Methanol
15. Giemsa stain B. Tissue Culture Supplies and Cell Lines
1. Tissue culture dishes (6-well clusters)
2. Chinese hamster ovary (CHO) cells, clone $K_1$-BH$_4$ (originally from Oakridge National Laboratory)

METHODS

A. Preparation
1. Media for cell growth (Ham's F-12)
   a. Add 50 ml of heat inactivated fetal bovine serum per 500 ml Ham's F-12 medium.
   b. Add 2.5 ml of glutamine per 500 ml medium.
2. Liver 59—cofactors mix
   a. Prepare stock solutions of: 0.M sodium phosphate, pH 8.0; 0.1M NADP; 1.0M glc-6-P; 1.5M potassium chloride; 0.5 M magnesium chloride; and 0.5M calcium chloride.
   b. Prepare sterile 8.8 ml cofactor mix aliquots containing: 5.45 ml double distilled water; 2.5 ml sodium phosphate; 0.4 ml NADP; 0.05 ml glc-6-P; 0.2 ml potassium chloride; and 0.2 ml magnesium chloride. These aliquots can be stored frozen at −70° C.
   c. Prior to use, thaw aliquot cofactor mix and add 0.2 ml calcium chloride. A white precipitate will form.
   d. Add 1 ml of liver S9 (−30 mg/ml) to the cofactor mix and store on ice.

B. Cytotoxicity Assay
1. Trypsinize CHO cells using the procedures described in Research Microbiology SOP TC-001.
2. Determine cell concentration using one of the procedures outlined in Research Microbiology SOP TC-002.
3. Dilute the cell suspension to a final concentration of 100 cells per ml in complete growth media. Maintain the cell suspension on ice until cells are plated to minimize cellular attachment to the surfaces of the container.
4. Pipet 2 ml of the cell suspension into each well (200 cells/well). Shake the dish in two directions immediately after filling all of the wells in the dish. This is critical to ensure even distribution of cells throughout the entire surface area of the dish.
5. Allow the cells to attach for 3 hours at 37° ±1° C. in a humidified incubator with an atmosphere of 5% $CO_2$ in air.
6. At the time of treatment, change medium to 2 ml Ham's F-12 medium (with glutamine, without serum).
7. For assays designed to measure the effect of metabolic activation, add 0.4 ml of S9-cofactors mixture to 1.6 ml of Ham's F-12 (with glutamine, without serum) at the time of treatment.
8. Add test compound in 20 μl of ethanol, acetone or DMSO (1% v/v final concentration of solvent) depending on solubility. Note: DMSO also facilitates cellular uptake. if the test compound is a suspension (such as liposomes) they can be added in up to 100 μl of PBS. Three wells are used per dose.
9. Each assay must include positive and negative controls. The equivalent volume of the solvent alone serves as the negative control. Any known cytotoxic agents at cytotoxic doses can be used as positive controls (e.g., cyclohexamide, mitomycin C, benzo (a) pyrene).

10. Return dishes to the incubator for 3 hours. Do not stack the dishes more than two high as it is important for sample cultures to stabilize at 37°±1° C. at the same time. This is even more critical for experiments involving S9 since the reaction kinetics for the enzymes involved in metabolic activation are temperature dependent.

11. Remove medium containing test compound out of each well and rinse surface with 1 ml of PBS per well.

12. Pipet 2 ml of complete growth medium (Ham's F-12, with serum and glutamine) into each well.

13. Return dishes to incubator and allow cells to grow for 7–8 days. Do not handle dishes as this minimizes colony splitting.

14. Fix, stain and score colonies as described in Research Microbiology SOP TC-005.

15. Express cytotoxicity data as cloning efficiency (C.E.) and relative survival (R.S.).

$$C.E. = \frac{\text{number of colonies}}{\text{number of cells plated (200)}}$$

$$R.S. = \frac{C.E. \text{ treated}}{C.E. \text{ solvent control}}$$

The results of the cytotoxicity assay or cytotoxicity profile are shown in FIG. 2, which shows the relative survival of the Chinese hamster ovary cells as a function of concentration of the formulation tested.

The hereinabove-described CHO clonal assay was used to establish the cytotoxicity profiles for the present invention preserved by five different preservative systems. Ten to one hundredfold dilutions of these solutions were tested, with all dilutions being made in distilled water. The unpreserved present invention was also tested. The vehicle, water in this case, was used as a positive control. The relative cell survival is calculated by comparing the cells surviving from a formulation with the cells surviving from water. Disodium monolaureth sulfosuccinate, a "mild" anionic surfactant commonly used in baby shampoos and lid hygiene products, was used as a negative control. The solutions tested were as follows:

1. Pluronic® P85/Pluronic® F87/octoxynol 40 (7:1:2 ratio) 10% solution
2. Pluronic® P85/Pluronic® F87/octoxynol 40 (7:1:2 ratio) 10% solution+Benzyl Alcohol (0.5%)
3. Pluronic® P85/Pluronic® F87/octoxynol 40 (7:1:2 ratio) 10% solution+Benzyl Alcohol (0.5%)+EDTA (0.05%)
4. Pluronic® P85/Pluronic® F87/octoxynol 40 (7:1:2 ratio) 10% solution+Benzyl Alcohol (0.5)+Germall 115 (0.3%)
5. Pluronic® P85/Pluronic® F87/octoxynol 40 (7:1:2 ratio) 10% solution+Dowicil® 200 (0.03%)–Phosphate Buffer
6. Disodium monolaureth sulfosuccinate The results dramatically show the low cytotoxicity of the formulations in accordance with the present invention. For example, at concentrations of up to 10% of the unpreserved formulation in accordance with the present invention, an 80% relative survival is shown, which is roughly 100 fold less cytotoxic than the "mild" surfactant, disodium monolaureth sulfosuccinate. The preserved formulations, depending on the preservatie system used, may be 30 to 100 fold less cytotoxic than disodium monolaureth sulfosuccinate. Therefore, because of the low cytotoxicity of the formulations in accordance with the present invention, the formulation need not be rinsed, or flushed, from the eye after instillation. This is to be compared with prior art products comprising anionic surfactants which must, because of their relatively high cytotoxicity, be rinsed, or removed, from the eye after instillation because residual anionic surfactant will cause eye irritation.

Hence, it can be readily appreciated that the low cytotoxicity of the formulation of the present inventions eliminates the criticality of rinsing.

That is, if some, or all, of the formulation of the present invention remains in the eye, little, if any, irritation occurs, due to the nonionic surfactants therein.

In addition, it is shown that a formulation in accordance with the present invention which is preserved with benzyl alcohol exhibited a cytotoxicity profile similar to the unpreserved solution at 10% of formulation. Also, the addition of EDTA did not significantly alter the cytotoxicity profile of the formulation at 10%.

Other formulations of various preservatives exhibited a lower cytotoxicity profile.

The formulation of the present invention may be produced in any conventional manner by combining the surfactants in the proportions hereinabove recited.

Although there has been hereinabove described a nonirritating detergent surfactant composition suitable for application in cleaning of sensitive tissues such as periocular and ocular tissues, in accordance with the present invention, for the purpose of illustrating the manner in which the invention may be used to advantage, it should be appreciated that the invention is not limited thereto. Accordingly, any and all modifications, variations, or equivalent arrangements which may occur to those skilled in the art, should be considered to be within the scope of the present invention as defined in the appended claims.

What is claimed is:

1. A nonirritating detergent surfactant composition suitable for application to and cleaning of sensitive tissue, said nonirritating detergent surfactant composition comprising:

a principal nonionic surfactant present in said nonirritating detergent surfactant composition in a sufficient amount to clean said sensitive tissue, said principal nonionic surfactant comprising a block copolymer of polyoxyethylene and polyoxypropylene;

a first auxiliary nonionic surfactant present in said nonirritating detergent surfactant composition in a sufficient amount to increase the cleaning ability of the principal nonionic surfactant, said first auxiliary nonionic surfactant comprising a block copolymer of polyoxyethylene and polyoxypropylene; and a second auxiliary nonionic surfactant present in said composition in a sufficient amount to increase the cleaning ability of the principal nonionic surfactant, said second auxiliary nonionic surfactant comprising an ethoxylated octyl phenol.

2. The nonirritating detergent surfactant composition according to claim 1 wherein the cleaning ability of the nonirritating detergent surfactant composition is greater than the cleaning ability of each of the principal and auxiliary nonionic surfactants.

3. The nonirritating detergent surfactant composition according to claim 1 or 2 wherein the cleaning ability is the lipid cleaning efficiency of the surfactants.

4. A nonirritating detergent surfactant composition having low cytotoxicity for the cleaning of ocular and periocular tissue, said nonirritating detergent surfactant composition comprising:

a principal nonionic surfactant present in said nonirritating detergent surfactant composition in a sufficient amount to clean ocular and periocular tissue, said principal nonionic surfactant comprising a block copolymer of polyoxyethylene and polyoxypropylene;

a first auxiliary nonionic surfactant present in said nonirritating detergent surfactant composition in a sufficient amount to increase the cleaning ability of the principal nonionic surfactant, said first auxiliary nonionic surfactant comprising a block copolymer of polyoxyethylene and polyoxypropylene; and a second auxiliary nonionic surfactant present in said composition in a sufficient amount to increase the cleaning ability of the principal nonionic surfactant, said second auxiliary nonionic surfactant comprising an ethoxylated octyl phenol.

5. The nonirritating detergent surfactant composition according to claim 4 wherein the cleaning ability of the nonirritating detergent surfactant composition is greater than the cleaning ability of each of the principal and auxiliary nonionic surfactants.

6. The nonirritating detergent surfactant composition according to claim 4 or 5 wherein the cleaning ability is the lipid cleaning efficiency of the surfactants.

7. The nonirritating detergent surfactant composition according to claim 4 or 5 wherein said principal and auxiliary nonionic surfactants are present in said nonirritating detergent surfactant composition in a combined amount of at most 10% by weight and when applied to Chinese hamster ovary cells, more than 80% of the cells survive at ten fold dilution in distilled water.

8. A nonirritating detergent surfactant composition having low cytotoxicity for ocular and periocular tissue, said nonirritating detergent surfactant composition comprising:

a principal; nonionic surfactant present in said nonirritating detergent surfactant composition in a sufficient amount to clean said sensitive tissue, said principal nonionic surfactant comprising a block copolymer of polyoxyethylene and polyoxypropylene;

a first auxiliary nonionic surfactant present in said nonirritating detergent surfactant composition in a sufficient amount to increase the cleaning ability of the principal nonionic surfactant, said first auxiliary nonionic surfactant comprising a block copolymer of polyoxyethylene and polyoxypropylene; and a second auxiliary nonionic surfactant present in said composition in a sufficient amount to increase the cleaning ability of the principal nonionic surfactant, said second auxiliary nonionic surfactant comprising an ethoxylated octyl phenol, said principal and auxiliary nonionic surfactants enabling the combination of the surfactant composition with positively or negatively charged preservatives, buffers and medicaments without chemical incompatability.

\* \* \* \* \*